United States Patent
Engelbreth

(10) Patent No.: US 9,931,481 B2
(45) Date of Patent: Apr. 3, 2018

(54) METERED DOSE INHALER APPLICATOR

(71) Applicant: TRUDELL MEDICAL INTERNATIONAL, London (CA)

(72) Inventor: Daniel Engelbreth, London (CA)

(73) Assignee: TRUDELL MEDICAL INTERNATIONAL (CA)

(*) Notice: Subject to any disclaimer, the term of this patent is extended or adjusted under 35 U.S.C. 154(b) by 814 days.

(21) Appl. No.: 14/212,461

(22) Filed: Mar. 14, 2014

(65) Prior Publication Data

US 2014/0318534 A1 Oct. 30, 2014

Related U.S. Application Data

(60) Provisional application No. 61/781,828, filed on Mar. 14, 2013.

(51) Int. Cl.
*A61M 11/04* (2006.01)
*A61M 11/08* (2006.01)
*A61M 15/00* (2006.01)

(52) U.S. Cl.
CPC ........ *A61M 15/0001* (2014.02); *A61M 11/04* (2013.01); *A61M 11/08* (2013.01); *A61M 15/009* (2013.01); *A61M 15/0065* (2013.01); *A61M 2205/276* (2013.01); *A61M 2205/586* (2013.01)

(58) Field of Classification Search
CPC .......... A61M 15/0021; A61M 15/0065; A61M 15/0081; A61M 15/0086; A61M 15/009; A61M 11/08; A61M 15/0001; A61M 11/04
See application file for complete search history.

(56) References Cited

U.S. PATENT DOCUMENTS

| | | |
|---|---|---|
| 3,405,843 A | 10/1968 | Watson, Jr. |
| 3,456,645 A | 7/1969 | Brock |
| 3,994,421 A * | 11/1976 | Hansen ............... A61M 15/009 128/200.23 |
| 4,077,548 A | 3/1978 | Beard |
| 4,079,862 A | 3/1978 | Fegley |
| 4,324,348 A | 4/1982 | Johnson et al. |
| 4,678,106 A | 7/1987 | Newell et al. |
| 4,860,738 A | 8/1989 | Hegemann et al. |

(Continued)

FOREIGN PATENT DOCUMENTS

| | | |
|---|---|---|
| DE | 4436051 A1 | 4/1996 |
| WO | WO 2010/007361 A1 | 1/2010 |

*Primary Examiner* — Valerie L Woodward
(74) *Attorney, Agent, or Firm* — Brinks Gilson & Lione

(57) ABSTRACT

A metered dose inhaler ("MDI") applicator is disclosed that includes a carrier, a housing, an adjuster and a lever. The carrier defines an aperture configured to receive a boot of a MDI. The housing is configured to be assembled with the carrier and to move in a vertical direction within the MID applicator relative to the carrier. The adjuster is configured to move between a locked position and an unlocked position, wherein when the adjuster is in the locked position, the adjuster is configured to prevent the carrier and the housing from moving in one or more directions relative to one another. The lever is pivotally connected to the housing and is configured to transfer a force applied to the lever to a canister of the MDI and to actuate the MDI to dispense an aerosolized medicine.

24 Claims, 22 Drawing Sheets

(56) References Cited

U.S. PATENT DOCUMENTS

| | | |
|---|---|---|
| 6,397,837 B1 | 6/2002 | Ferris |
| 6,681,763 B2 | 1/2004 | Ferris |
| 2002/0073992 A1 | 6/2002 | Andersson |
| 2005/0022806 A1* | 2/2005 | Beaumont ......... A61M 15/0065 128/200.14 |
| 2006/0137681 A1* | 6/2006 | Von Hollen ........ A61M 15/009 128/200.14 |
| 2013/0139814 A1* | 6/2013 | Mullane ............ A61M 15/0086 128/203.12 |
| 2013/0239957 A1* | 9/2013 | Pinfold ................. A61M 11/04 128/200.23 |

* cited by examiner

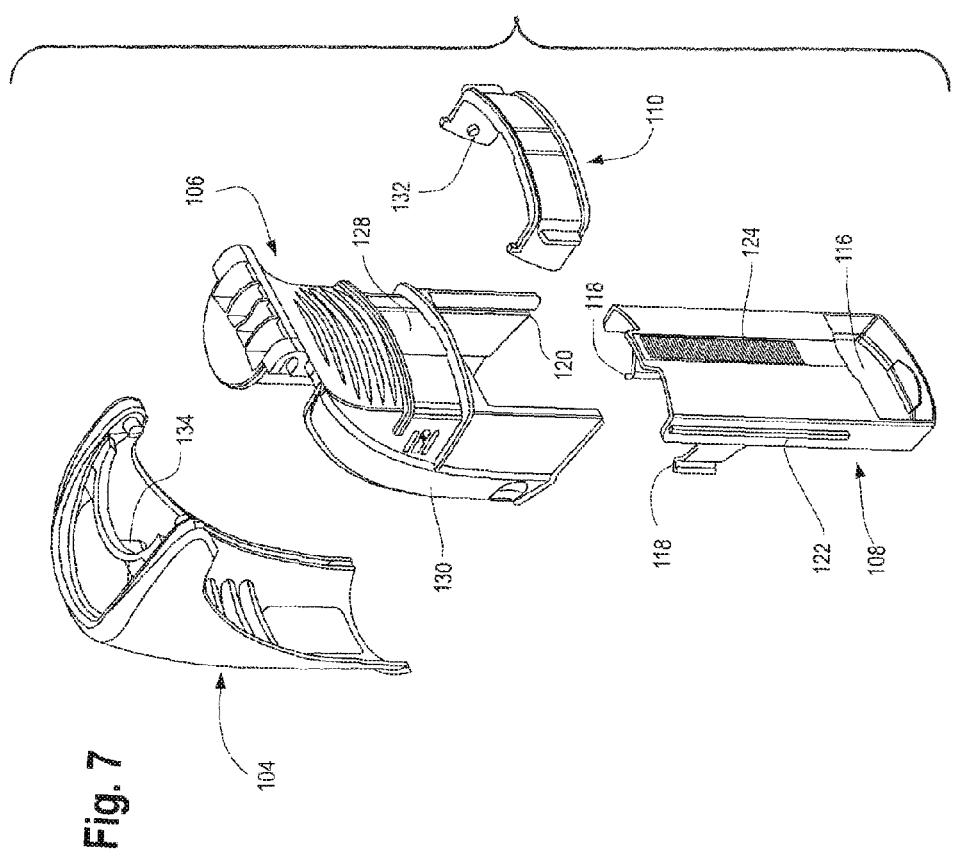

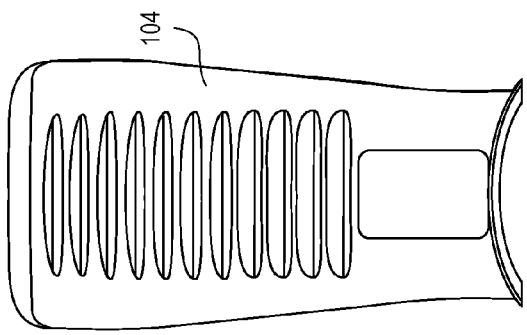
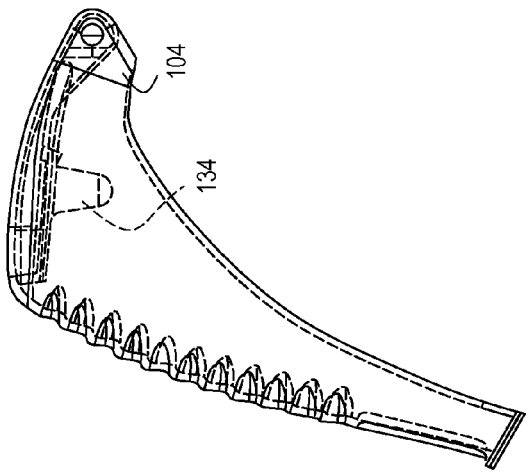
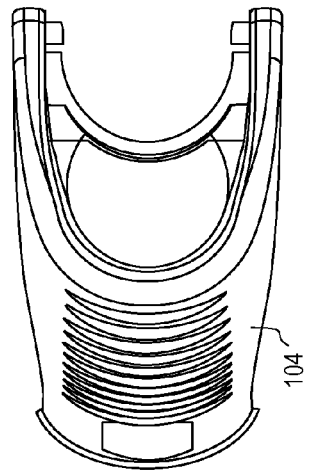
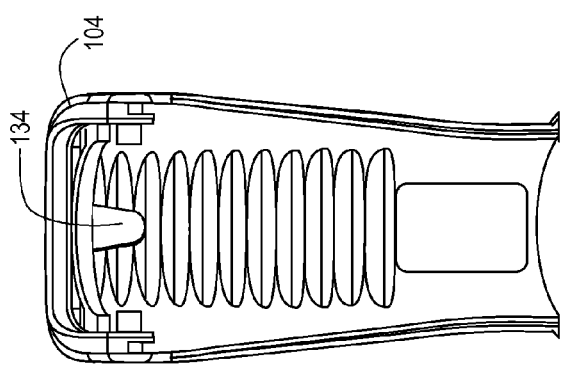

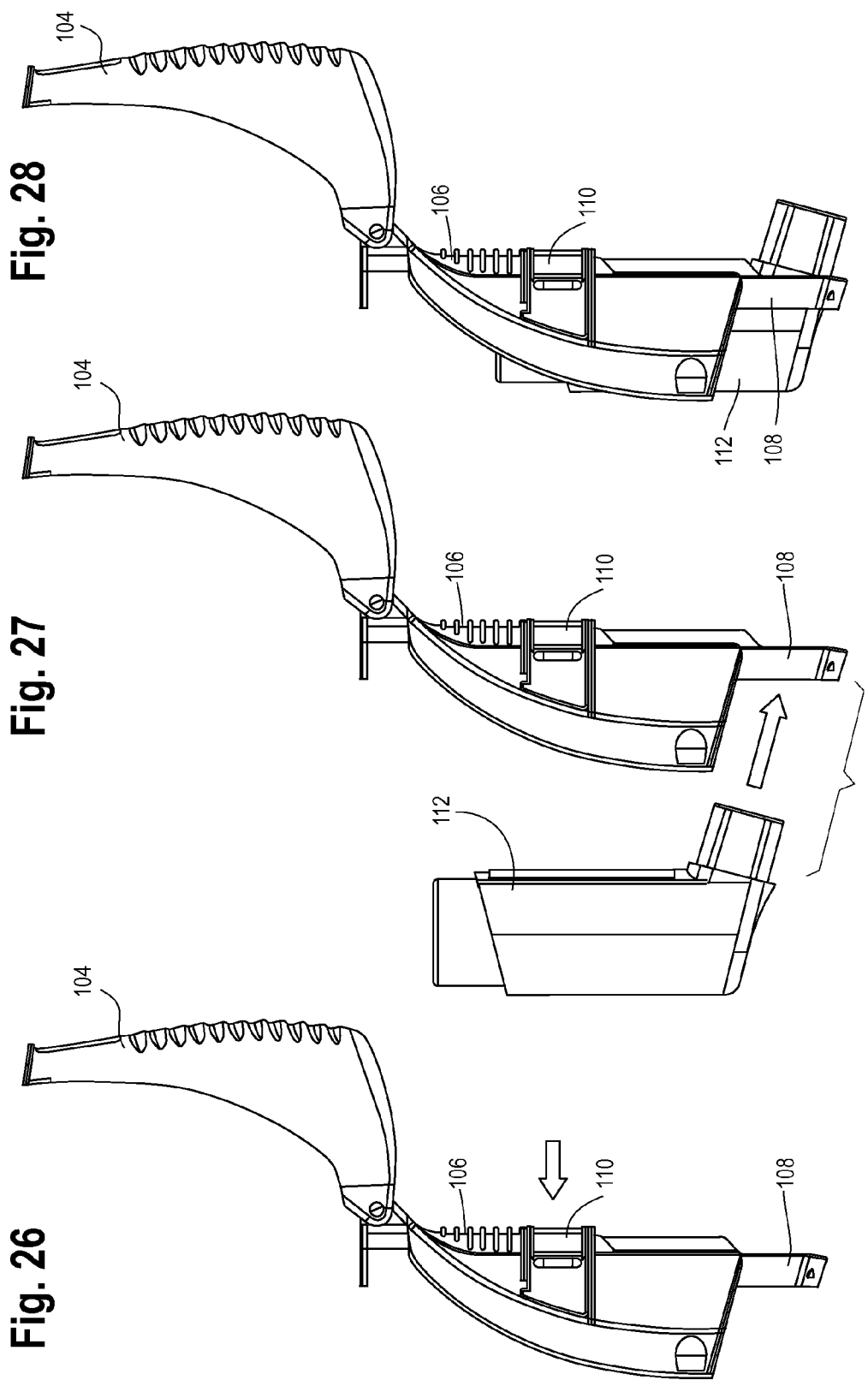

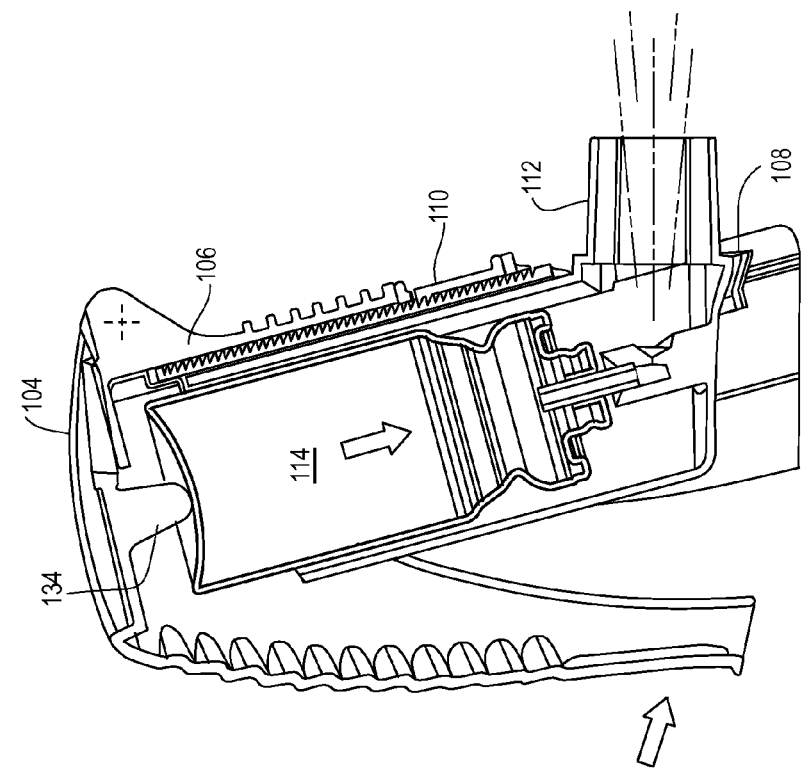
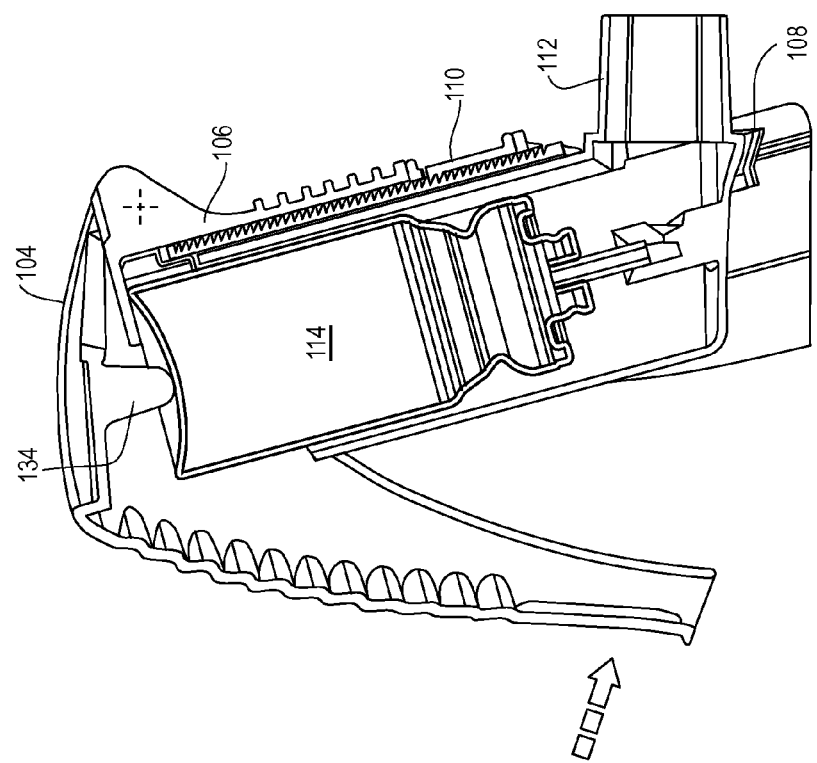

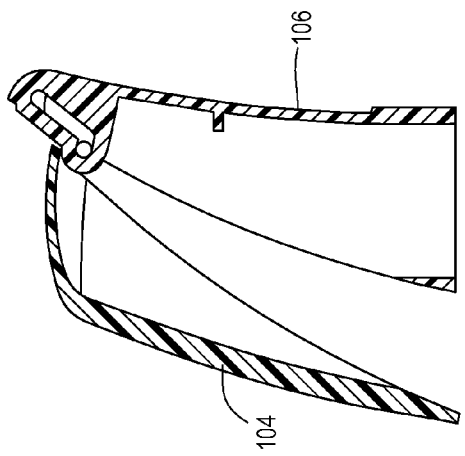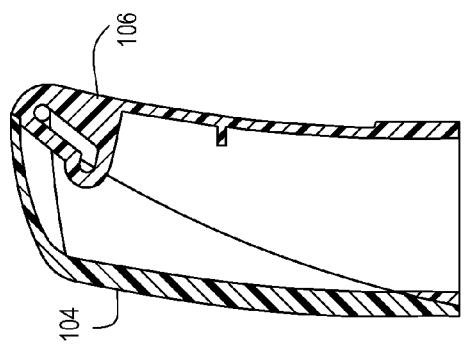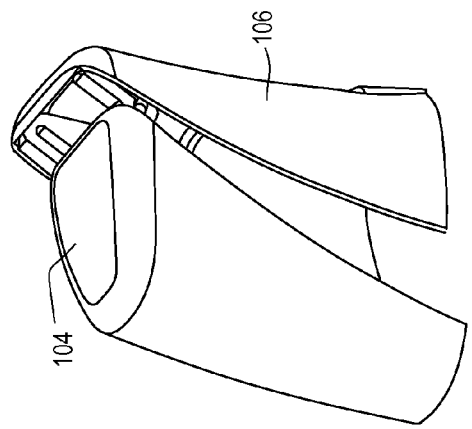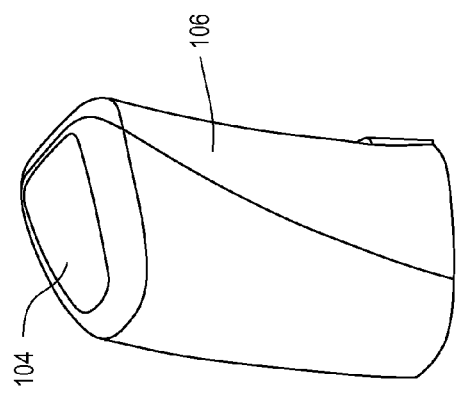

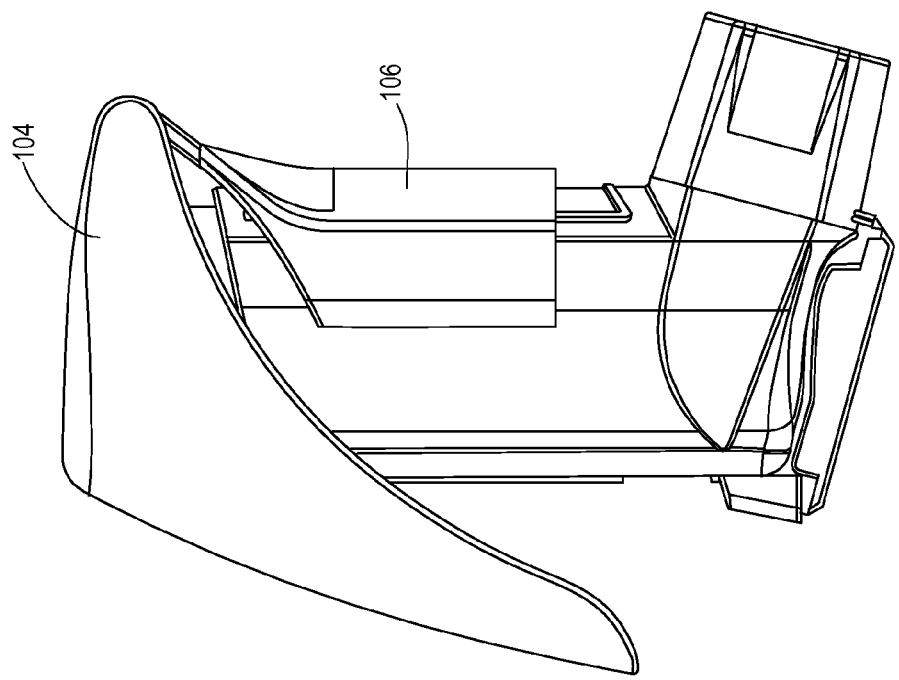
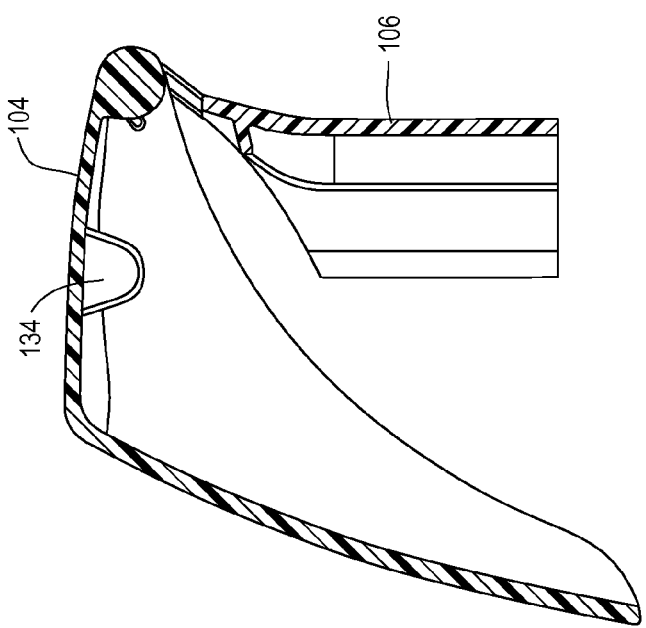

METERED DOSE INHALER APPLICATOR

This application claims the benefit of U.S. Provisional Application No. 61/781,828, filed Mar. 14, 2013, the entire disclosure of which is hereby incorporated herein by reference.

BACKGROUND

Metered dose inhalers (MDI) are devices that produce aerosolized medicines. Physicians generally use a MDI to deliver a specific amount of medicine to the lungs of a patient. The MDI produces a burst of aerosolized medicine, which the patient then inhales.

A MDI typically includes a canister, a metering valve, and an actuator. The canister holds a pressurized medicine, the metering valve restricts an amount of medicine that is dispensed when the MDI is actuated, and the actuator, that typically includes a stem and nozzle in communication with the metering valve, provide the ability to dispense a limited amount of medicine from the canister and metering valve in an aerosolized from.

Patients may have difficulty actuating a MDI or storing a MDI in a manner that prevents inadvertent actuations. Accordingly, improved applicators for use with a MDI that provide the ability to easily actuate the MDI and that provide for convenient storage of the MDI are desirable.

BRIEF DESCRIPTION OF THE DRAWINGS

FIG. 7 is an exploded view of the MDI applicator of FIG. 2.

FIG. 8 is a front view of a lever of the MDI applicator of FIG. 2.

FIG. 9 is a side view of the lever of the MDI applicator of FIG. 2.

FIG. 10 is a rear view of the lever of the MDI applicator of FIG. 2.

FIG. 11 is a top view of the lever of the MDI applicator of FIG. 2.

FIGS. 24-35 are drawings illustrating a procedure for positioning a metered dose inhaler in the MDI applicator of FIG. 2 and utilizing the MDI applicator to dispense aerosolized medicine.

FIGS. 40A, 40B, 41A, and 41B are drawings illustrating a two-position lever of a MDI applicator.

FIGS. 44-49 illustrate additional implementations of a MDI applicator.

DETAILED DESCRIPTION OF THE DRAWINGS

Figure 1:
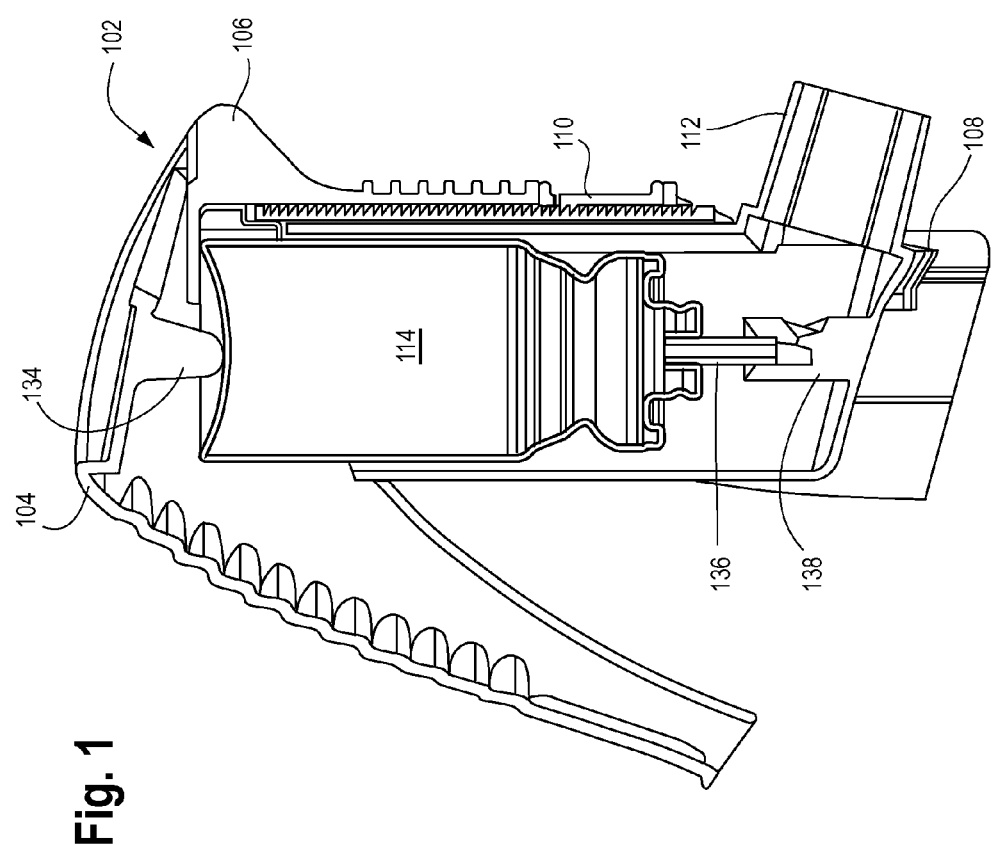
FIG. 1 is cross-sectional view of one implementation of a metered dose inhaler (MDI) positioned in a MDI applicator.
Figure 3:
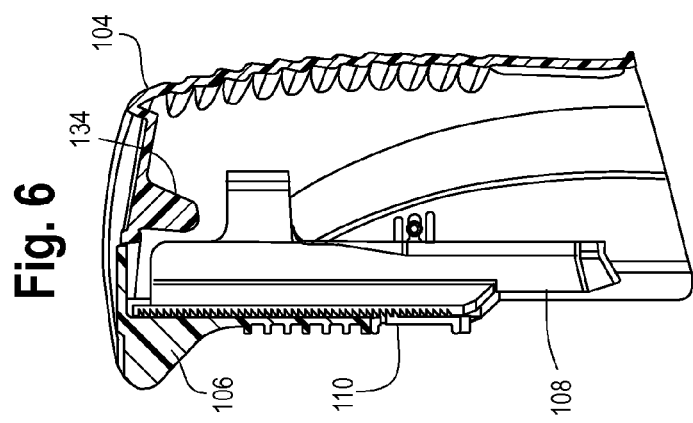
FIG. 3 is a rear view the MDI applicator of FIG. 2.
Figure 5:
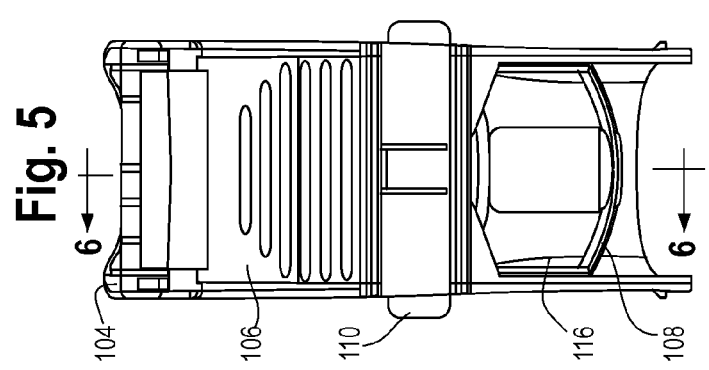
FIG. 5 is a front view of the MDI applicator of FIG. 2.
Figure 4:
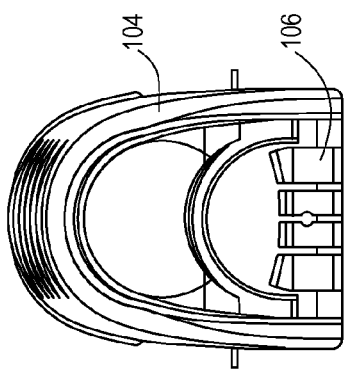
FIG. 4 is a top view of the MDI applicator of FIG. 2.
Figure 6:
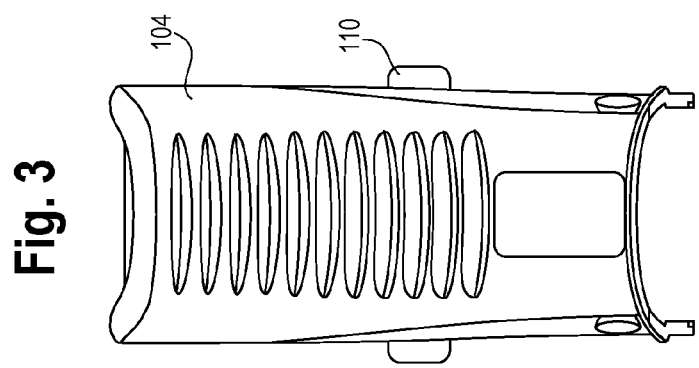
FIG. 6 is a cross-sectional view of the MDI applicator taken along line 6-6 of FIG. 5.
Figure 2:
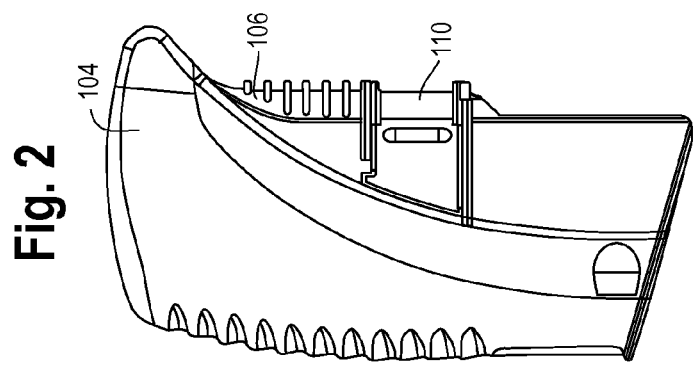
FIG. 2 is a side view of one implementation of a MDI applicator.
Figure 14:
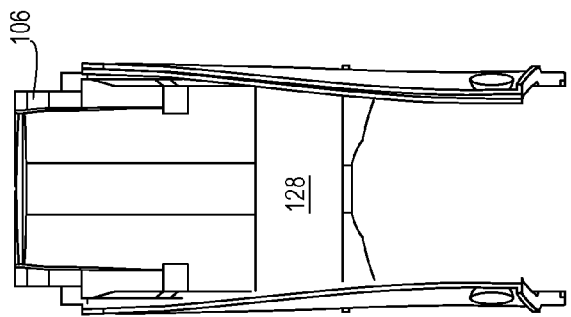
FIG. 14 is a rear view of the housing of the MDI applicator of FIG. 2.
Figure 13:
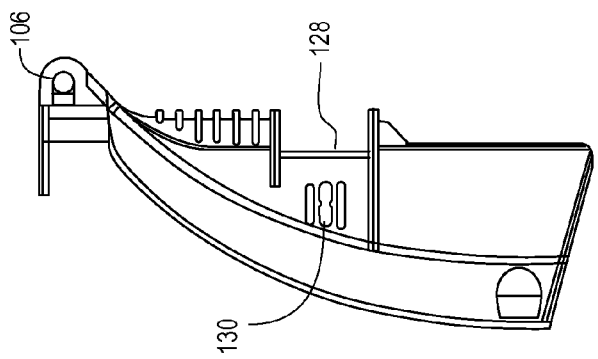
FIG. 13 is a side view of the housing of the MDI applicator of FIG. 2.
Figure 12:
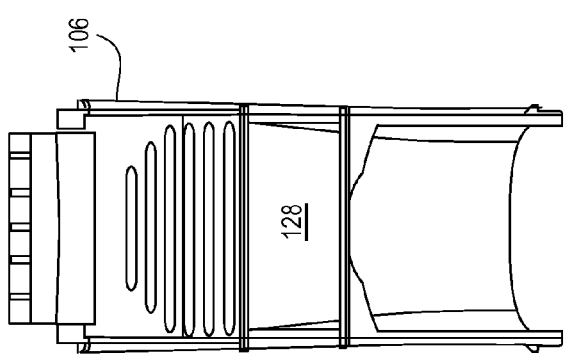
FIG. 12 is a front view of a housing of the MDI applicator of FIG. 2.
Figure 15:
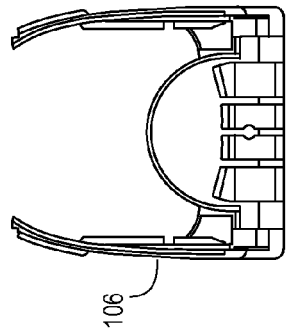
FIG. 15 is a top view of the housing of the MDI applicator of FIG. 2.
Figure 16:
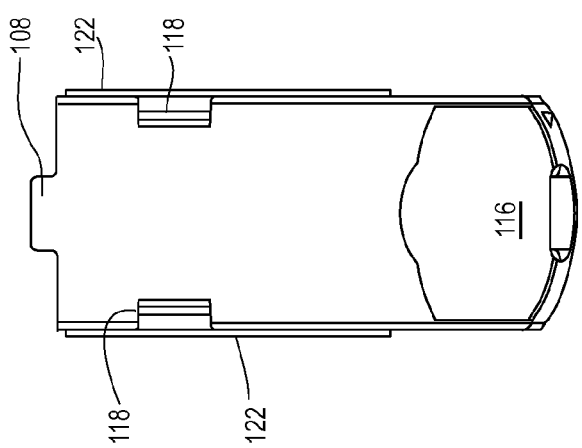
FIG. 16 is a front view of a carrier of the MDI applicator of FIG. 2.
Figure 17:
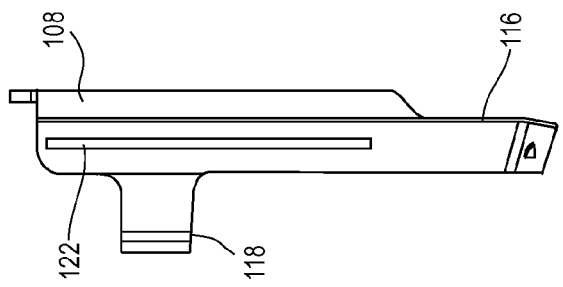
FIG. 17 is a side view of the carrier of the MDI applicator of FIG. 2.
Figure 18:
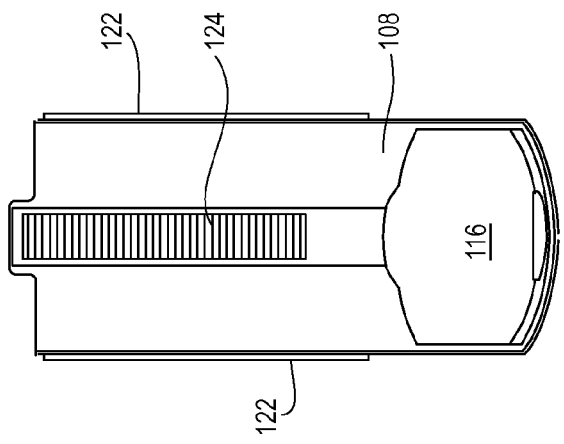
FIG. 18 is a rear view of the carrier of the MDI applicator of FIG. 2.
Figure 19:
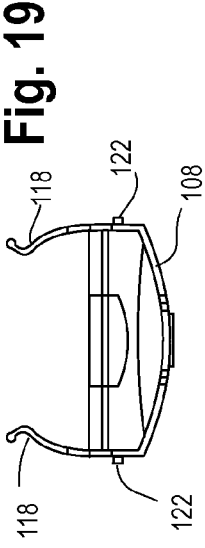
FIG. 19 is a top view of the carrier of the MDI applicator of FIG. 2.
Figure 20:
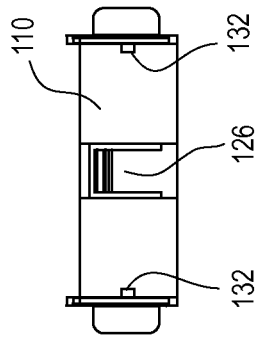
FIG. 20 is a front view of an adjuster of the MDI applicator of FIG. 2.
Figure 21:
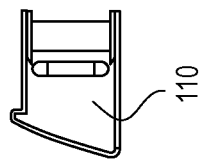
FIG. 21 is a side view of the adjuster of the MDI applicator of FIG. 2.
Figure 22:
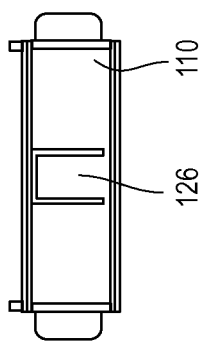
FIG. 22 is a rear view of the adjuster of the MDI applicator of FIG. 2
Figure 23:
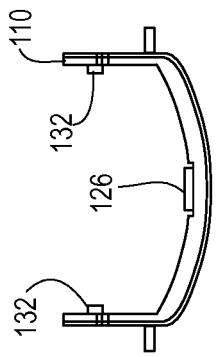
FIG. 23 is a top view of the adjuster of the MDI applicator of FIG. 2.

The present disclosure is directed to a metered dose inhaler (MDI) applicator that provides a lever to assist a patient in actuating a MDI. FIG. 1 is a cross-sectional view of one implementation of a MDI 112 positioned in a MDI applicator 102. The MDI applicator 102 may include a lever 104, a housing 106, a carrier 108, and an adjuster 110.

As explained in more detail below, the lever 104 is positioned on the MDI applicator 102 such that when a force is applied to the lever 104 of the MDI applicator 102, the lever 104 transfers the force to a canister 114 of the MDI 112 positioned in the MDI applicator 102. When sufficient force is applied to the canister 114 of the MDI 112 via the lever 104, the MDI 112 dispenses an aerosolized medicine that a patient may inhale.

FIGS. 3-6 illustrate various views of the MDI applicator 102; FIG. 7 illustrates an exploded view of the MDI applicator 102; FIGS. 8-11 illustrate various views of the lever 104 of the MDI applicator 102; FIGS. 12-15 illustrate various views of the housing 106 of the MDI applicator 102; FIGS. 16-19 illustrate various views of the carrier 108 of the MDI applicator 102; and FIGS. 20-23 illustrate various views of the adjuster 110 of the MDI applicator 102.

Referring to FIG. 7, the carrier 108 defines an aperture 116 that is dimensioned to receive a boot of a MDI. When the carrier 108 receives the boot of the MDI, the boot of the MDI passes through the carrier 108 in a telescopic manner. In some implementations, the carrier 108 may include one or more prongs 118 positioned on either side of the carrier 108. The prongs 118 are configured to engage with the MDI and to secure the carrier 108, and the MDI applicator 102 as a whole, to the MDI.

The housing 106 and the carrier 108 are configured to be assembled to one another in the MDI applicator 102. In some implementations, the housing 106 and the carrier 108 are configured to move in relation to one another in a vertical manner so that the MDI applicator 102 may accommodate MDIs of various heights.

To assist in the relative movement between the housing 106 and the carrier 108, in some implementations the housing 106 may define one or more guide channels 120 and the carrier 108 may define one or more guide tabs 122. When the housing 106 and the carrier 108 are assembled, the guide tabs 122 of the carrier 108 are positioned in the guide channels 120 of the housing 106 to restrict movement between the housing 106 and the carrier 108 to vertical movement.

As will be explained in more detail below, when a MDI is positioned within the MDI applicator 102, the housing 106 and the carrier 108 are adjusted in a vertical manner to accommodate the height of the MDI. After the housing 106 and the carrier 108 are adjusted to the proper height, the adjuster 110 locks the position of the housing 106 relative to the carrier 108 to prevent further movement.

In some implementations, the carrier 108 defines a set of teeth 124 and the adjuster 110 defines a complementary set of teeth 126. Further, the housing 106 defines an aperture 128 such that as the housing 106 and the carrier 108 move relative to each other, at least a portion of the set of teeth 124 defined by the carrier 108 is exposed.

The adjuster 110 is positioned on housing 106 and is configured to move between a locked position and an unlocked position. In some implementations, when the adjuster 110 is in the locked position, the teeth 126 of the adjuster 110 engage the portion of the teeth 124 of the carrier 108 positioned in the aperture 128 of the housing 106. When the complementary sets of teeth 124, 126 engage, the engaged teeth restrict the vertical movement between the housing 106 and the carrier 108. In some implementations, the engaged teeth 124, 126 restrict movement in all directions such that the vertical height of the MDI applicator 102 may not be reduced or increased. However, in other implementations, the engaged teeth only restrict movement in a direction such that the height of MDI applicator 102 may be reduced, but not increased.

In some implementations, the adjuster 110 may move in a horizontal direction relative to the housing 106 to move from the locked position to the unlocked position. It will be appreciated that to move the adjuster 110 into the unlocked position, the adjuster 110 is moved away from the housing 106. Moving the adjuster 110 away from the housing 106 moves the teeth 126 of the adjuster 126 away from the teeth 124 of the carrier 108 that are positioned in the aperture 128 of the housing 106. Because the teeth 124 of the carrier 108 are no longer engaged with the teeth 126 of the adjuster 110, the housing 106 and the carrier 108 are free to move in a vertical direction relative to each other.

In some implementations, to assist the adjuster 110 in moving in a horizontal direction relative to the housing 106, the housing may define one or more guide channels 130 and the adjuster 110 may define one or more guide posts 132. When the housing 106 and the adjuster 110 are assembled, the guide posts 132 of the adjuster 110 are positioned within the one or more guide channels 130 of the housing 106 to restrict movement of the adjuster 110 with respect to the housing 106 to a horizontal direction.

The lever 104 is pivotally connected to the housing 106 at an end of the housing 106 such that a user may place a force on the lever to cause the lever to move towards the housing 106. In one implementation, the lever defines a post 134 on an underside of the lever. However, in other implementations, the lever may define a protrusion having a shape other than a post.

Referring to FIG. 1, when the MDI 112 is positioned within the MDI applicator 102, the post 134 of the lever 104 is positioned against an end of the canister 114 of the MDI 112. Generally, when a force is applied to the lever 104 of the MDI applicator 102, the pivotal movement of the lever 104 and the post 134 transfers the force applied to the lever 104 to a downward force against the canister 114 of the MDI 112. When the downward force against the canister 114 of the MDI 112 causes a stem 136 of the MDI 112 to compress enough to open an internal valve of the MDI 112, medicine within the canister passes through the stem 136 and out of a nozzle 138 of the MDI 112 in an aerosolized form for inhalation by a patient.

Figure 24:
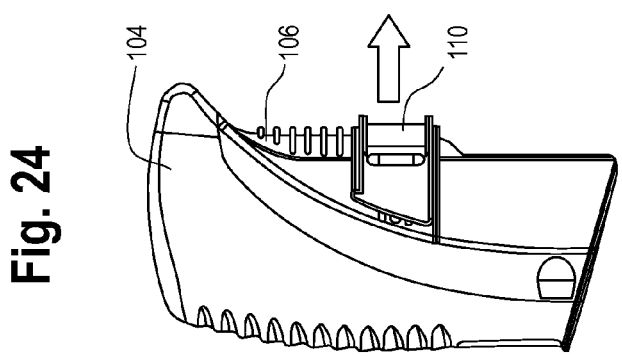

FIGS. 24-35 are drawings illustrating a procedure for positioning a metered does inhaler in the MDI applicator and utilizing the MDI applicator to dispense aerosolized medicine. As shown in FIG. 24, the adjuster 110 is moved away from the housing 106 and into an unlocked position. As discussed above, moving the adjuster 110 into the unlocked position allows the housing 106 and the casing 108 to move in a vertical direction relative to one another in order to accommodate MDI's of various sizes.

Figure 25:
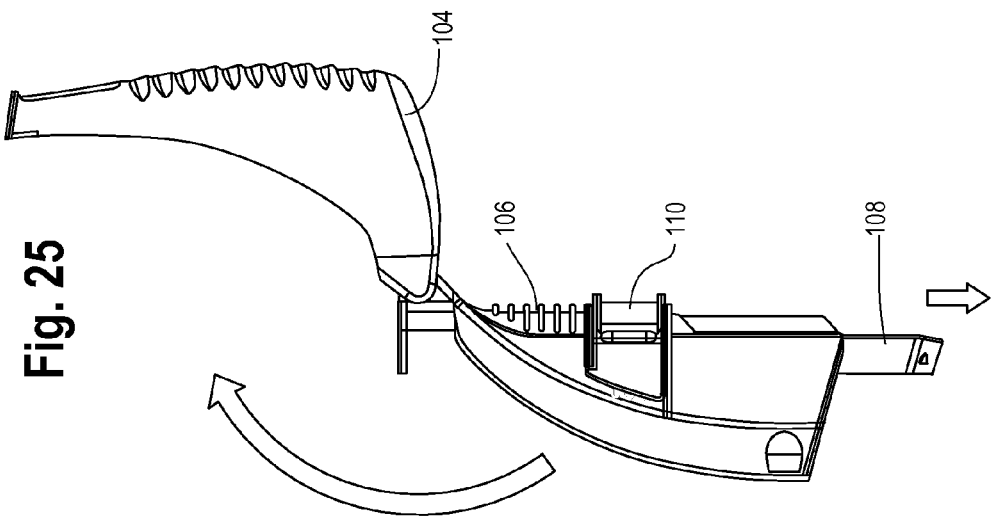

As shown in FIG. 25, the carrier 108 is pulled down relative to the housing 106. In some implementations the housing 106 and the carrier 108 may include one or more stops in order to prevent the housing and 106 and the carrier 108 from separating. The lever 104 is additionally pivoted to an open position so that the MDI applicator 102 is configured to receive the MDI 112.

As shown in FIG. 26, once the carrier 108 is pulled down relative to the housing 106, the adjuster 110 is moved towards the housing 106 and into the locked position. As discussed above, moving the adjuster 110 into the locked position restricts movement between the housing 106 and the carrier 108 in one or more directions.

Figure 29:
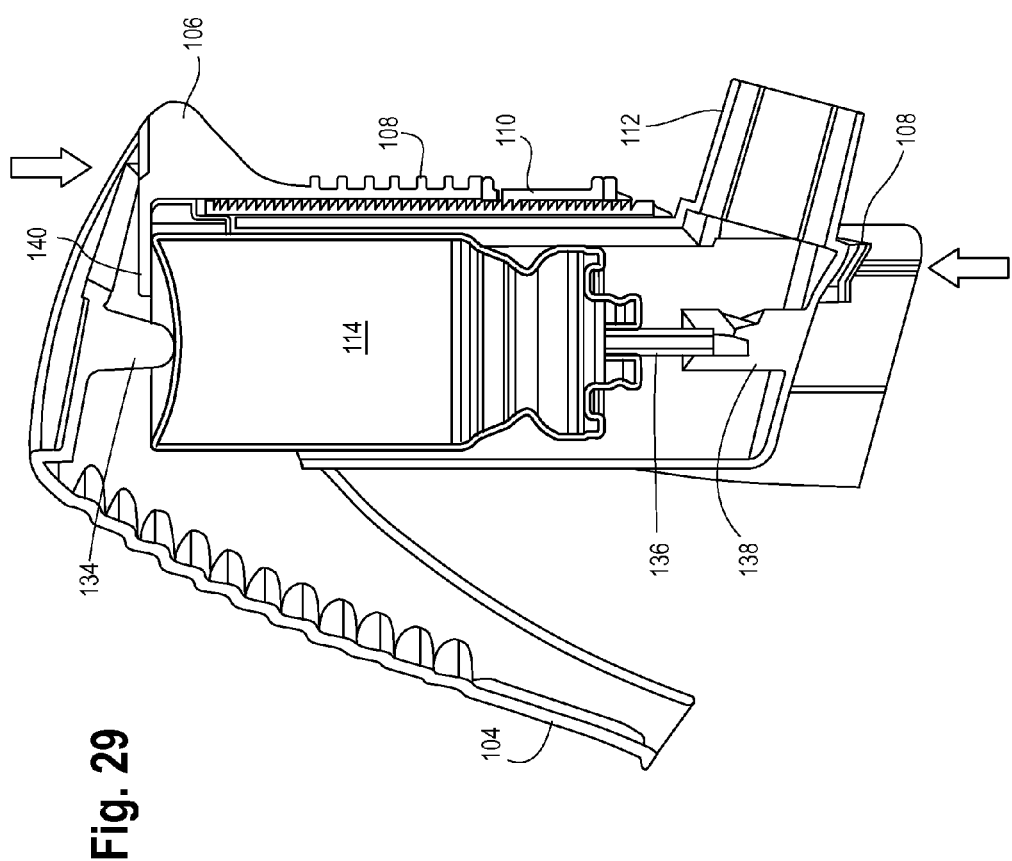

As shown in FIGS. 27 and 28, the MDI 112 is inserted into the aperture 116 of the carrier 108. Once the boot of the MDI 112 is fully seated in the carrier 108, the housing 106 and the carrier 108 are compressed as shown in FIG. 29 to reduce the height of the MDI applicator 102. In some implementations, the housing 106 and the carrier 108 are compressed until a ledge 140 of the housing 106 comes in contact with the canister 114 of the MDI 112.

Figure 31:
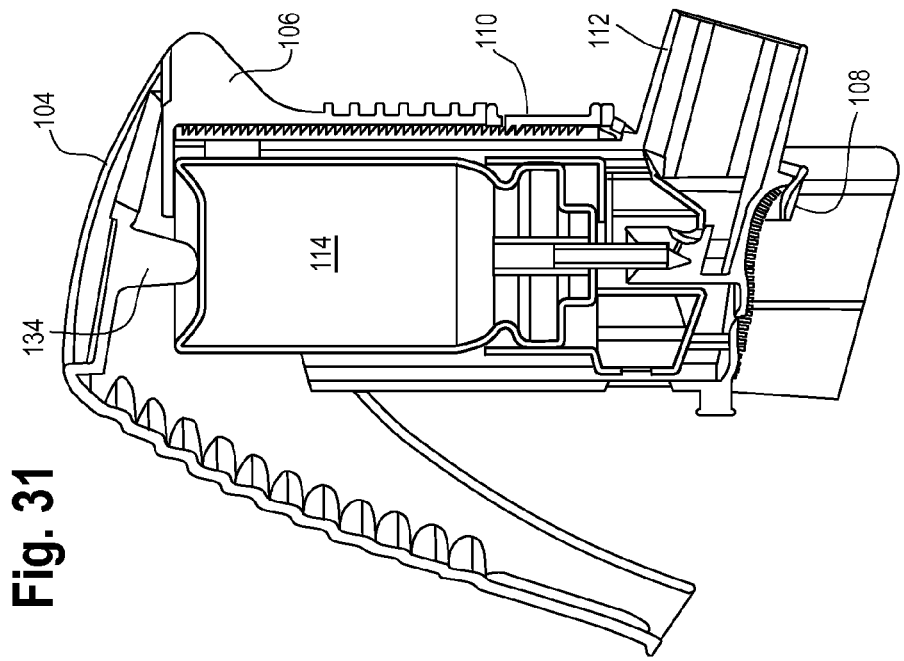
Figure 30:
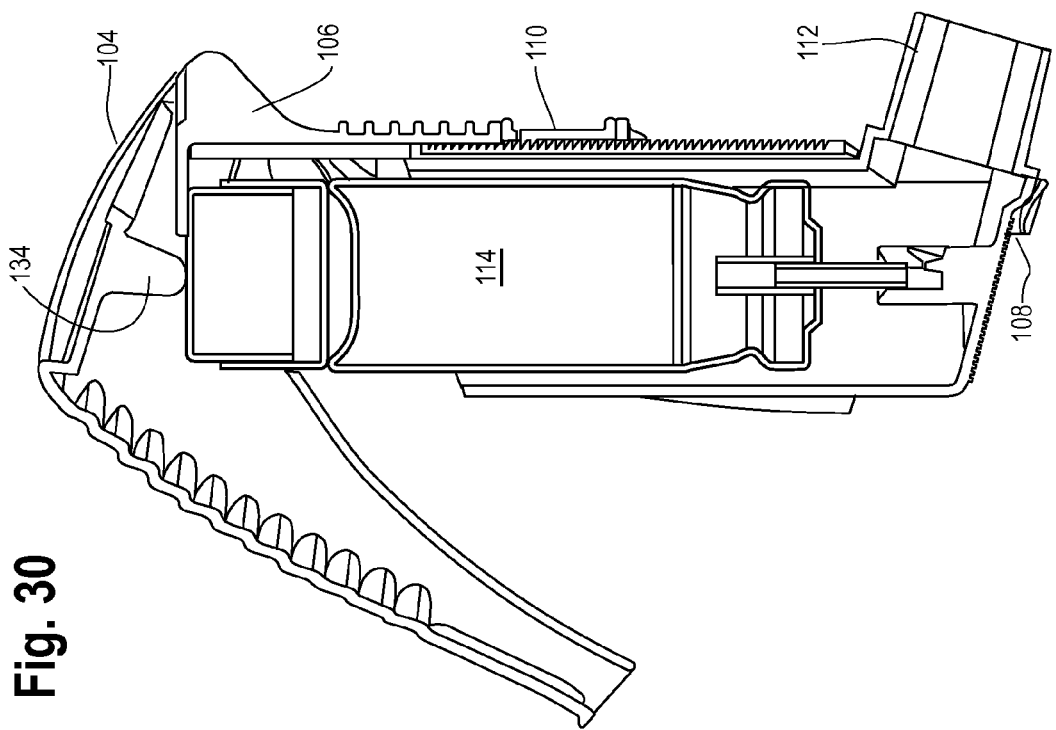
Figure 33:
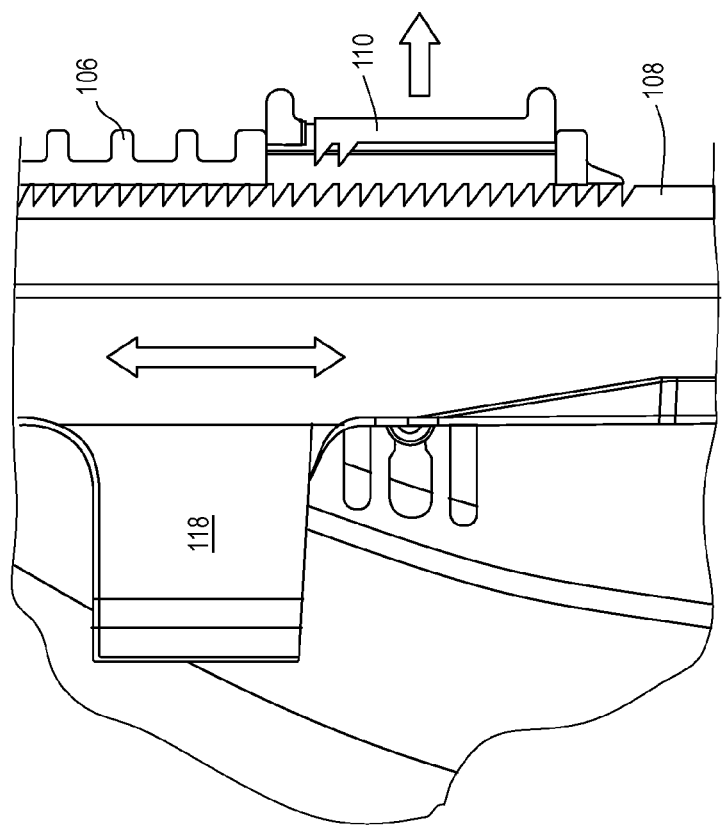
Figure 32:
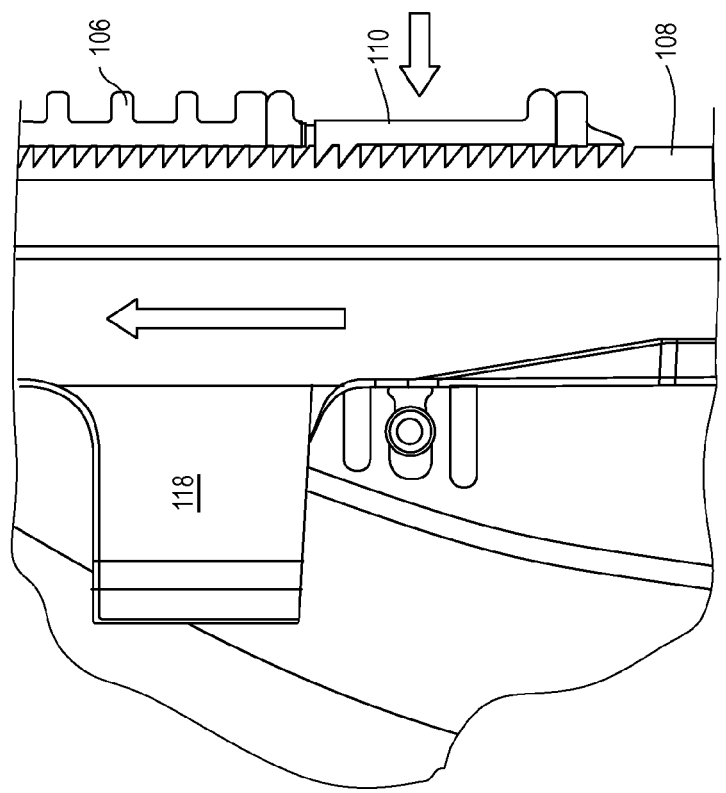

It will be appreciated that the process of adjusting a distance between the housing 106 and the carrier 108 provides the MDI applicator 102 the ability to accommodate MDI's of various heights, as shown in FIGS. 30 and 31.

In some implementations, the distance between the housing 106 and the carrier 108 must be adjusted while the adjuster 110 is in the unlocked position. However, in other implementations, such as those shown in FIGS. 32 and 33, a distance between the housing 106 and the carrier 108 may be adjusted while the adjuster 110 is in the locked position. In these implementations, the teeth 124 of the carrier 108 and the complementary teeth 126 of the adjuster 110 are configured to allow a user to reduce the distance between the housing 106 and the carrier 108 while preventing the user from increasing the distance between the housing 106 and the carrier 108.

Referring to FIGS. 34 and 35, once the height of the MDI applicator 102 is adjusted to properly accommodate the MDI 112, a user may apply a force to the lever 104. Because the MDI 112 is securely positioned in the carrier 108, as the lever 104 pivotally moves towards the housing 106 and the carrier 108, the post 134 of the lever 104 applies a downward force on the canister 114 of the MDI 112. When the stem 136 of the MDI 112 is compressed enough to open an internal valve, a pressurized medication solution is released from the canister 114 through the stem 136. The medication solution is released into the nozzle 138 where it forms an aerosol plume as it enters the atmosphere.

Figure 37:
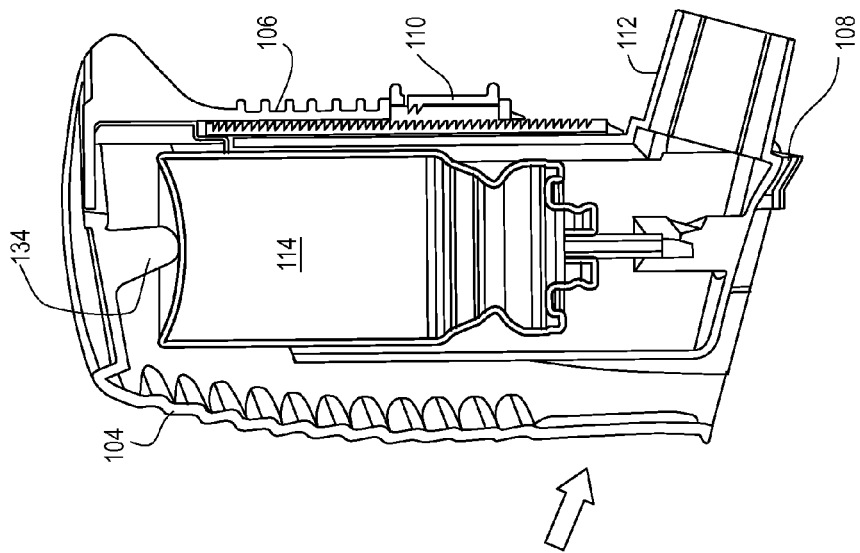
FIGS. 36 and 37 are drawings illustrating a procedure for placing a MDI applicator in a storage configuration.
Figure 36:
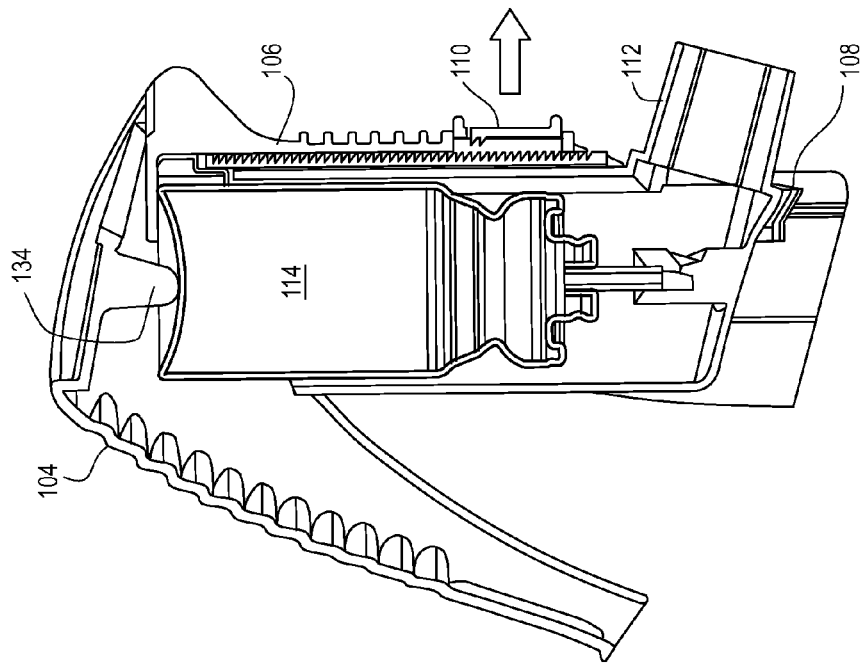

When the MDI applicator 102 is not in use, the MDI applicator 102 may be moved into a storage position that prevents a user from inadvertently actuating the MDI 112. As shown in FIGS. 36 and 37, to move the MDI applicator 102 into a storage position, the user first moves the adjuster 110 into an unlocked position. Placing the adjuster 110 in the unlocked position allows the housing 106 and the carrier 108 to move freely in a vertical direction with respect to one another.

After moving the adjuster 110 into the unlocked position, the user may place a force on the lever 104 to bring the lever against the housing 106 as shown in FIG. 37. Because the housing 106 and the carrier 108 may move freely in a vertical direction with respect to one another, as the post 134 of the lever 104 presses against the canister 114 of the MDI 112, the force on the lever 104 causes the housing 106 to move away from the carrier 108 and the height of the MDI applicator 102 to increase. Further, it will be appreciated that because the force on the lever 104 causes the housing 106 to move away from the carrier 108, the force on the lever 104 does not additionally cause the stem 136 of the MDI 112 to compress. After moving the lever 104 into a closed position, a user may then move the adjuster 110 into the locked position to lock the lever 104 against the housing 106 and the carrier 108.

Figure 39:
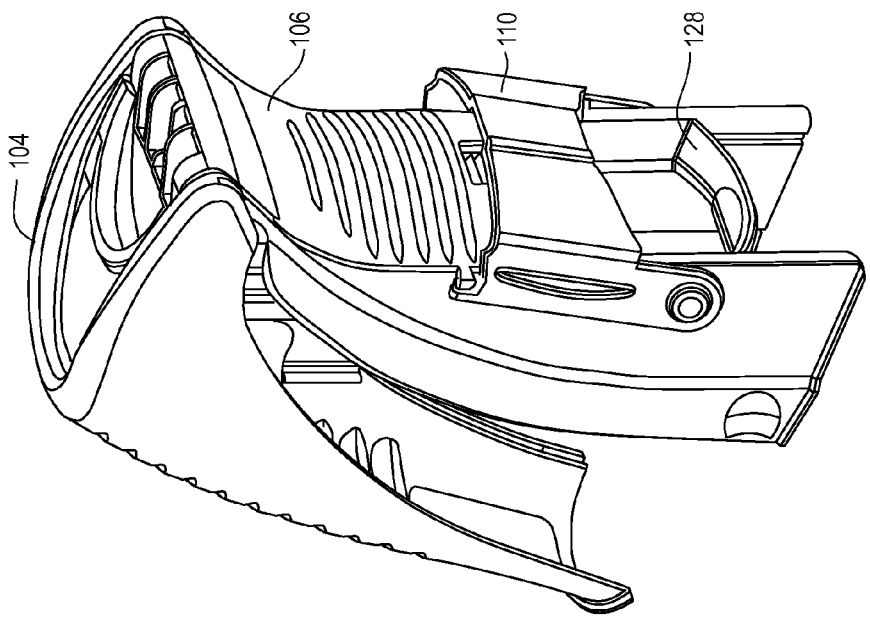
FIGS. 38 and 39 are drawing illustrating another implementation of a MDI applicator with a pivoting adjuster.
Figure 38:
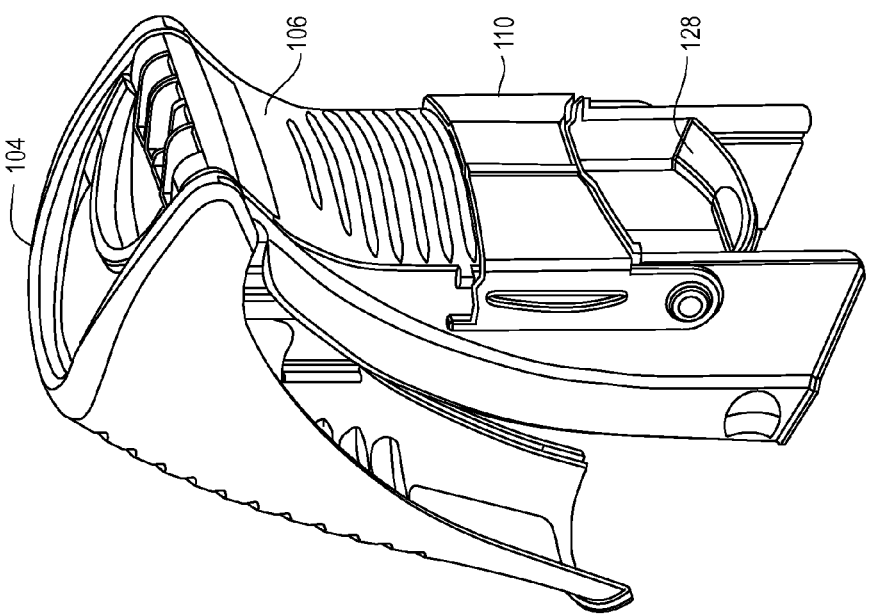

FIGS. 38 and 39 illustrate another implementation of a MDI applicator 102. In the MDI applicator of FIGS. 38 and 39, the adjuster 110 is a pivot adjuster that may be pivoted between a locked and an unlocked position.

FIGS. 40A, 40B, 41A, and 41B are drawings illustrating a two-position lever 104 of a MDI applicator 102. As shown in FIGS. 40A and 40B, the two-position lever 104 provides for the lever 104 to be in a first position when the MDI applicator 102 is in a closed position. However, when the MDI applicator 102 is in use, the lever 104 slides to a second position as shown in FIGS. 41A and 41B to provide more leverage in creating a downward force against the canister 114 of a MDI 112. It will be appreciated that a MDI applicator 102 with a two-position lever 104 may provide for a more compact MDI applicator 102 when not in use.

Figure 42:
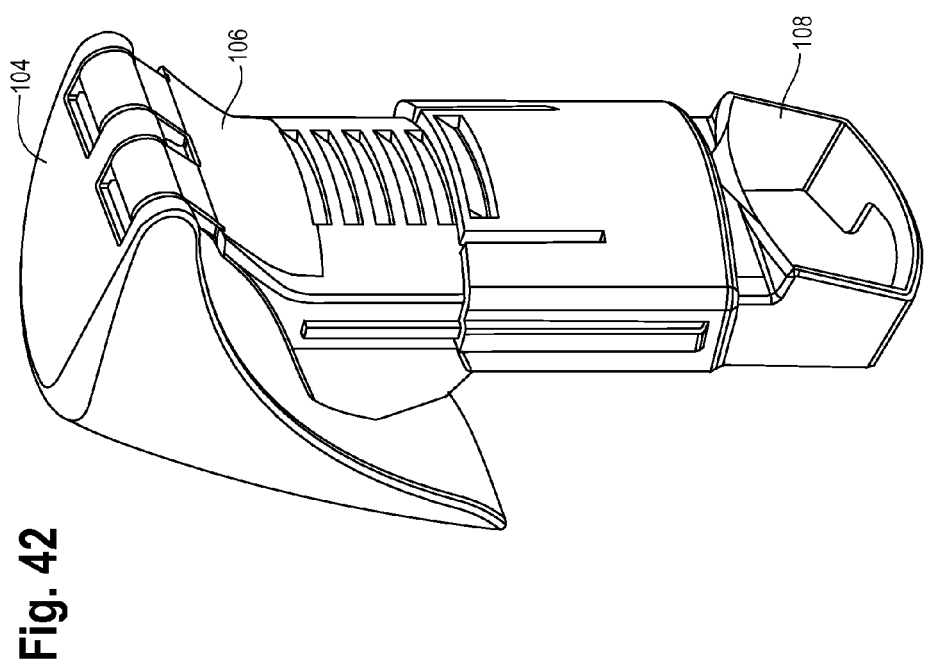
FIG. 42 is an illustration of another implementation of a MDI applicator.

FIG. 42 is an illustration of another implementation of a MDI applicator 102. In this implementation, the MDI applicator 102 does not include an adjuster 110 that may be moved between a locked and an unlocked position. Instead, the housing 106 and the carrier 108 are in telescopic communication with each other such that the housing 106 and the carrier 108 may be locked into discrete positions.

Figure 43:
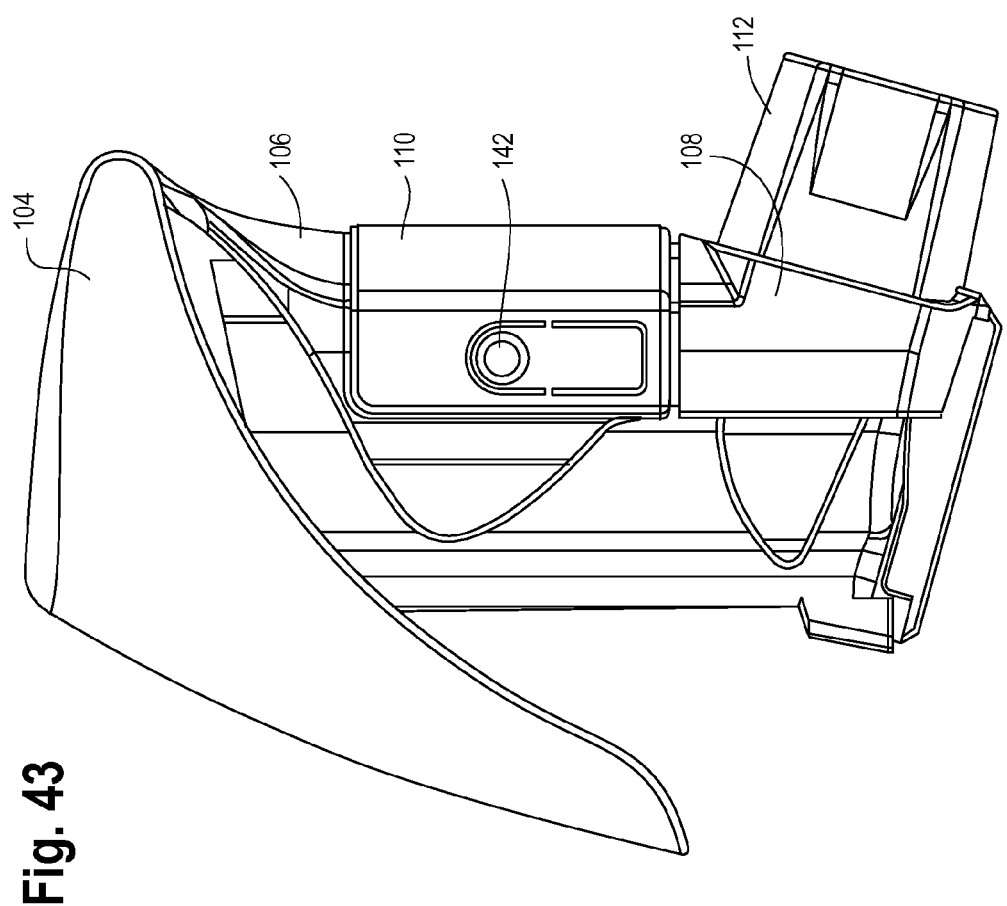
FIG. 43 is an illustration of yet another implementation of a MDI applicator.
Figure 45:
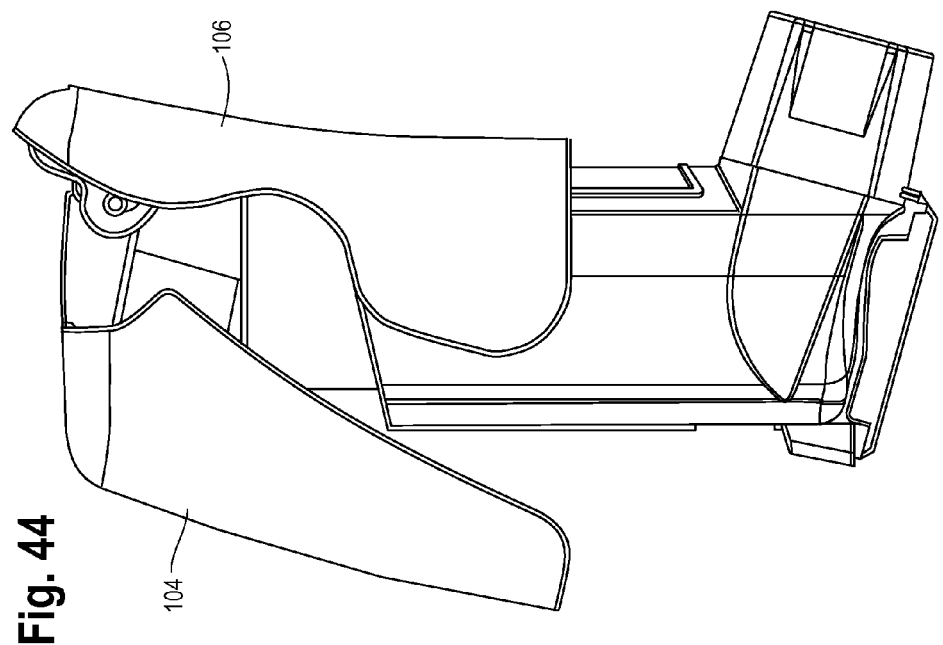
Figure 44:
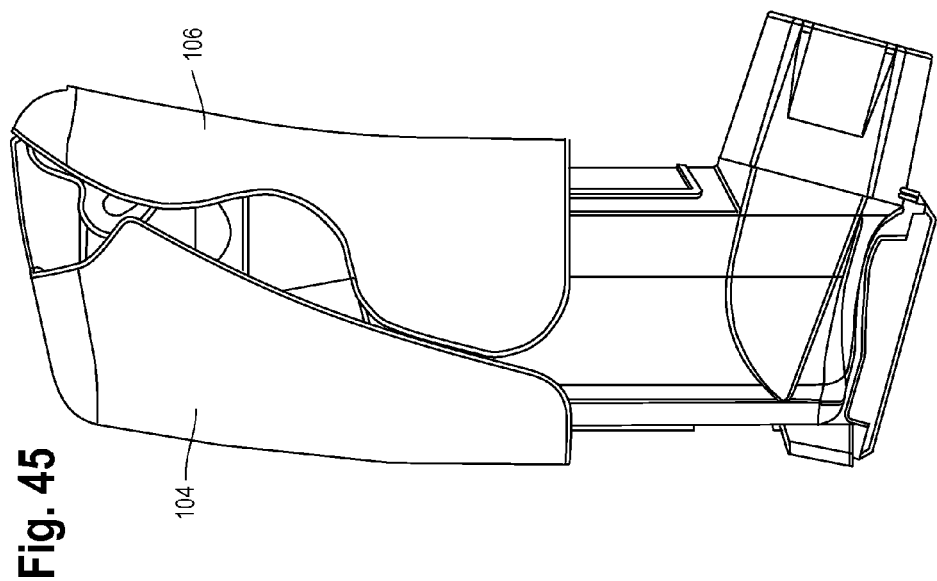
Figure 49:
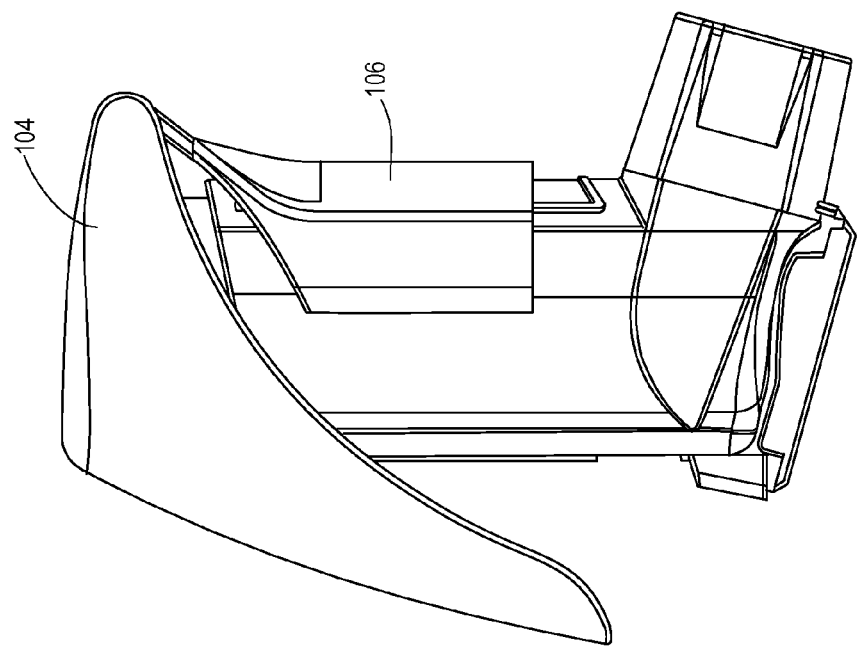
Figure 48:
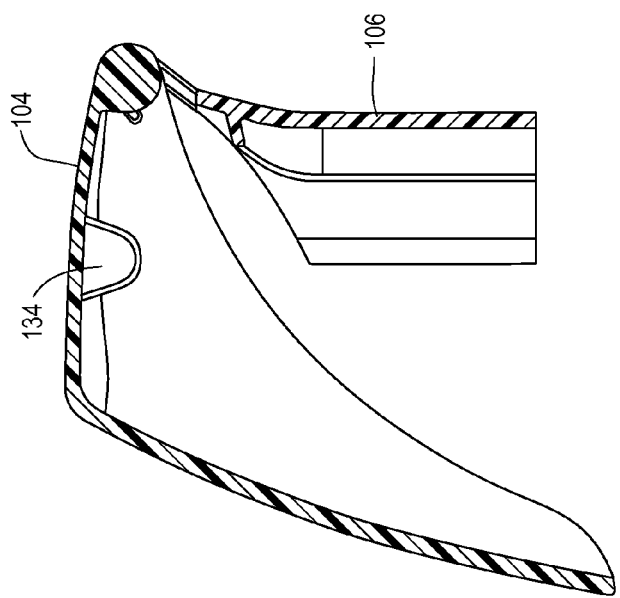

FIG. 43 is an illustration of yet another implementation of a MDI applicator. In the illustrated implementations, the adjuster 110 is an adjustment rack that may be moved between a locked and an unlocked position by means of aide spring levers 142.

FIGS. 44-49 illustrate further implementations of a MDI applicator 102. In the illustrated implementations, the MDI applicator 102 does not include a carrier 108 and an adjuster 110. Instead, the housing 106 is secured to a boot of a MDI 112 through the use of an adhesive such as double-sided tape or a hook and loop attachment system. The lever 104 is pivotally connected to the housing 106 as described above.

Figure 50A:
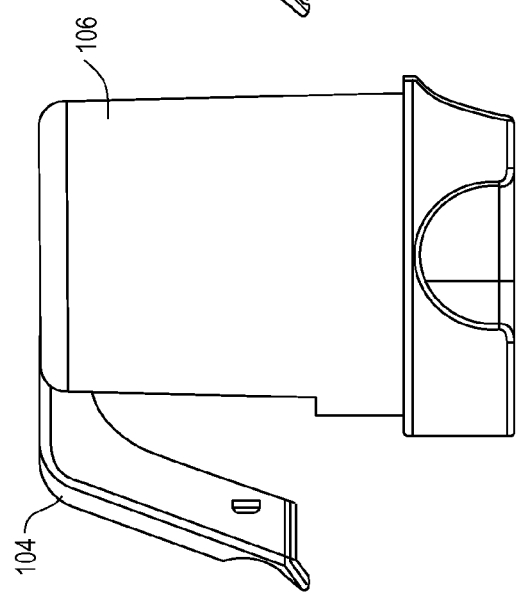
FIGS. 50A, 50B, and 50C illustrate another implementation of a MDI applicator.
Figure 50B:
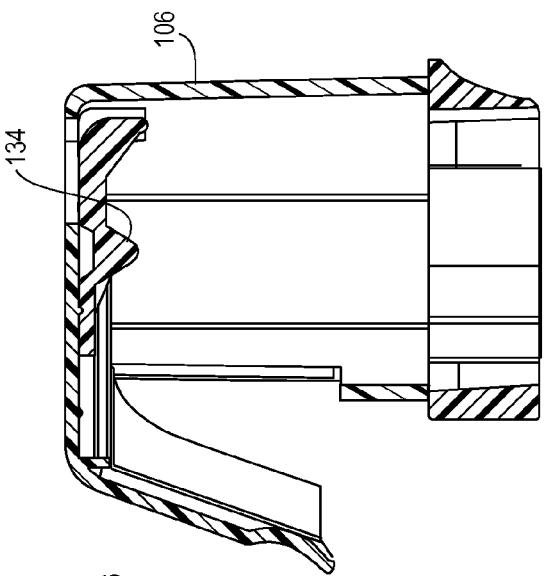
Figure 50C:
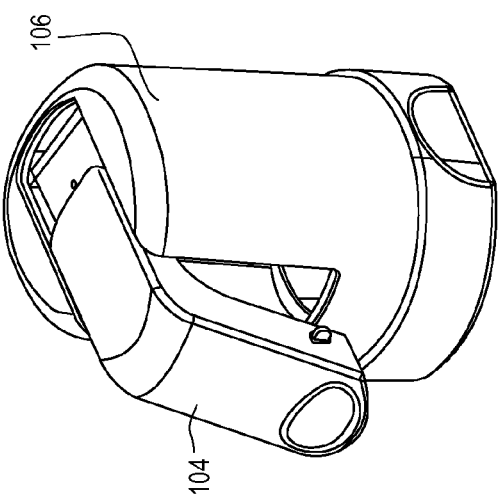

FIGS. 50A, 50B, and 50C illustrate another implementation of a MDI applicator. In the implementation of FIGS. 50A, 50B, and 50C, the MDI applicator includes a lever 104 and a circular housing 106. The circular housing is configured to receive a canister 114 of a MDI 112 and secure the housing 106 against the MDI 112. Additionally, the housing 106 and lever 104 are configured to position the canister against the post 134 of the lever 104 when the housing 106 receives the canister 114 of the MDI 112.

The lever 104 may move between two positions. In a first position, the lever 104 is extended away from the housing 106. When the lever 104 is in the first position, the lever 104 operates similar to described above. When a force is applied to the lever 104, the post 134 of the lever 104 transfers the force into a downward force against the canister 114 of the MDI 112. Because the housing 106 is secured to the MDI 112, the downward force against the canister 114 causes the MDI 112 to actuate and release aerosolized medicine.

In a second position, the lever 104 is moved towards the housing 106 and locked for storage. It will be appreciated that when the lever 104 is in a locked position, the lever may not transfer a force to actuate the MDI 112.

FIGS. 1-50 illustrate implementations of MDI applicators that provide a lever to assist a patient in actuating a MDI. The lever transfers forces applied to the lever to a canister of a MDI, thereby causing the MDI to dispense aerosolized medicine for inhalation by a patient.

The embodiments of the invention disclosed herein are presently considered to be preferred, various changes and modifications can be made without departing from the spirit and scope of the invention. As noted, the discussion above is descriptive, illustrative and exemplary and is not to be taken as limiting the scope defined by any appended claims, and all changes that come within the meaning and range of equivalents are intended to be embraced therein.

What is claimed is:

1. A metered dose inhaler ("MDI") applicator comprising:
   a carrier defining an aperture opening in a first direction and configured to receive a boot of a MDI;
   a housing moveably coupled to the carrier, wherein the housing and the carrier are moveable relative to one another in a second direction transverse to the first direction;
   a lever pivotally connected to the housing; and
   an adjuster moveably coupled to the housing, wherein the adjuster is moveable relative to the housing between a locked position and an unlocked position, wherein when the adjuster is in the locked position the adjuster is engaged with the carrier and restricts movement in at least one direction between the carrier and the housing.

2. The MDI applicator of claim 1, wherein the adjuster defines at least one tooth and the carrier defines a complementary set of teeth, and wherein the at least one tooth engages at least a portion of the set of teeth of the carrier when the adjuster is in the locked position.

3. The MDI applicator of claim 1 wherein the housing and carrier are moveable relative to each other in a first direction, and wherein the adjuster is moveable relative to the housing in a second direction perpendicular to the first direction.

4. The MDI applicator of claim 1 wherein the adjuster is pivotally connected to the housing.

5. The MDI applicator of claim 1 wherein the adjuster is translatably connected to the housing.

6. The MDI applicator of claim 5 wherein the housing comprises a track and the adjuster comprises a guide member moveable within the track.

7. The MDI applicator of claim 1 wherein the carrier is translatably connected to the housing.

8. The MDI applicator of claim 1 wherein the lever comprises a downwardly extending protrusion.

9. The MDI applicator of claim 1 further comprising a canister disposed in the housing.

10. The MDI applicator of claim 9 wherein the canister contains a medicine.

11. The MDI applicator of claim 1 wherein the carrier and housing are telescopically connected.

12. The MDI applicator of claim 1 wherein the first and second directions are substantially orthogonal.

13. A metered dose inhaler ("MDI") applicator comprising:
   a carrier defining an aperture configured to receive a boot of a MDI;
   a housing moveably coupled to the carrier, wherein the housing and the carrier are moveable in a vertical direction relative to one another;
   a lever pivotally connected to the housing; and
   an adjuster moveably coupled to the housing, wherein the adjuster is moveable relative to the housing between a locked position and an unlocked position, wherein when the adjuster is in the locked position, the carrier is moveable in one direction relative to the housing thereby allowing a height of the MDI applicator to decrease.

14. A metered dose inhaler ("MDI") applicator comprising:
   a carrier defining an aperture configured to receive a boot of a MDI;
   a housing moveably coupled to the carrier, wherein the housing and the carrier are moveable in a vertical direction relative to one another;
   an adjuster moveably coupled to the housing, wherein the adjuster is moveable relative to the housing between a locked position and an unlocked position, wherein when the adjuster is in the locked position the adjuster is engaged with the carrier and restricts movement in at least one direction between the carrier and the housing;
   a lever pivotally connected to the housing; and
   a canister holding a medicine disposed in the housing, wherein the lever is positionable against an end of the canister.

15. A metered dose inhaler ("MDI") applicator comprising:
   a carrier defining an aperture configured to receive a boot of a MDI;
   a housing moveably coupled to the carrier, wherein the housing and the carrier are moveable in a vertical direction relative to one another, wherein the carrier is translatably connected to the housing, and wherein the housing comprises a track and the carrier comprises a guide member moveable within the track; and
   a lever pivotally connected to the housing.

16. A metered dose inhaler ("MDI") applicator comprising:
   a carrier defining an aperture opening in a first direction and configured to receive a boot of a MDI;
   a housing moveably coupled to the carrier, wherein the housing and the carrier are moveable relative to one another in a second direction transverse to the first direction; and
   a lever pivotally connected to the housing, wherein the pivotal connection between the lever and the housing is slideable between spaced apart first and second positions.

17. A method of using a metered dose inhaler ("MDI") applicator comprising:
   inserting a portion of a MDI in a first direction through an aperture of a carrier and engaging the MDI with the carrier;
   moving the carrier and MDI in a second direction relative to a housing to a desired position, wherein the second direction is transverse to the first direction;
   locking the carrier to the housing such that the carrier and MDI may not be moved relative to the housing in a direction opposite the second direction; and
   engaging an end of the MDI with a lever pivotally connected to the housing.

18. The method of claim 17 wherein the locking the carrier to the housing comprises moving an adjuster relative to the housing from a first position wherein the adjuster is not engaged with the carrier to a second position wherein the adjuster is engaged with the carrier.

19. The method of claim 18 wherein the adjuster defines at least one tooth and the carrier defines a complementary set of teeth, and wherein moving the adjuster relative to the housing to the second position comprises engaging at least a portion of the set of teeth of the carrier with at least one tooth of the adjuster.

20. The method of claim 18 wherein moving the adjuster relative to the housing comprises moving the adjuster relative to the housing in a third direction perpendicular to the second direction.

21. The method of claim 18 wherein the housing comprises a track and the adjuster comprises a guide member, and wherein moving the adjuster relative to the housing comprises translating the adjuster relative to the housing by moving the guide member within the track.

22. The method of claim 17 wherein the MDI comprises an actuator boot having a housing portion defining a cavity extending in the second direction and a mouthpiece portion extending in the first direction from the housing portion, and a container disposed in the cavity of the housing portion of the actuator boot, wherein the mouthpiece portion is inserted in the first direction through the aperture of the carrier, and wherein the container defines the end of the MDI.

23. The method of claim 22 further comprising pivoting the lever relative to the housing, and thereby moving the container relative to the boot in the second direction and dispensing a dose of medicament from the container.

24. The method of claim 17 further comprising moving the carrier and MDI in the second direction relative to the housing after locking the carrier to the housing and thereby decreasing a height of the MDI applicator.

* * * * *